(12) United States Patent
Kiessling et al.

(10) Patent No.: US 12,156,368 B2
(45) Date of Patent: Nov. 26, 2024

(54) BRAKING RESISTOR ARRANGEMENT IN A COMPUTED TOMOGRAPHY GANTRY

(71) Applicant: Siemens Healthcare GmbH, Erlangen (DE)

(72) Inventors: Florian Kiessling, Forchheim (DE); Ulrich Kuehn, Baiersdorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 249 days.

(21) Appl. No.: 17/850,813

(22) Filed: Jun. 27, 2022

(65) Prior Publication Data
US 2023/0007811 A1     Jan. 5, 2023

(30) Foreign Application Priority Data

Jun. 30, 2021  (DE) .................... 10 2021 206 842.1

(51) Int. Cl.
| | |
|---|---|
| *H05K 7/20* | (2006.01) |
| *A61B 6/00* | (2006.01) |
| *A61B 6/03* | (2006.01) |
| *H02P 3/06* | (2006.01) |

(52) U.S. Cl.
CPC ......... *H05K 7/20172* (2013.01); *A61B 6/035* (2013.01); *A61B 6/4447* (2013.01); *H02P 3/06* (2013.01)

(58) Field of Classification Search
CPC . H05K 7/20172; G01N 23/046; G01N 23/083
See application file for complete search history.

(56) References Cited

U.S. PATENT DOCUMENTS

| | | | |
|---|---|---|---|
| 6,491,428 B1* | 12/2002 | Takanashi ............... | A61B 6/035 378/199 |
| 2004/0228450 A1* | 11/2004 | Mueller ............... | A61B 6/4488 378/199 |
| 2013/0340165 A1* | 12/2013 | Dong ..................... | A61B 6/032 5/601 |
| 2016/0174920 A1* | 6/2016 | Lacey .................. | A61B 6/4488 378/189 |
| 2017/0156688 A1* | 6/2017 | Tian ....................... | A61B 6/032 |
| 2018/0059270 A1* | 3/2018 | Hefetz ................... | A61B 6/035 |
| 2020/0315057 A1 | 10/2020 | Kuehn et al. | |

FOREIGN PATENT DOCUMENTS

| | | |
|---|---|---|
| DE | 19704338 A1 | 8/1998 |
| DE | 102014204794 A1 | 9/2015 |
| DE | 102019204501 A1 | 10/2020 |

* cited by examiner

*Primary Examiner* — Hugh Maupin
(74) *Attorney, Agent, or Firm* — Harness, Dickey & Pierce, P.L.C.

(57) ABSTRACT

A gantry for a computed tomography device has a support structure, a pivot bearing, a rotating frame, a first braking resistor configured to electromotively brake a rotational movement of the rotating frame, and a heat conductor configured to dissipate heat from the first braking resistor. A heat conductor and a pressure duct wall are interconnected to form a heat-conductor-to-pressure-duct-wall connection that is detachable, form-fitting, planar, and thermally conductive. The heat is transferrable from the first braking resistor to the airflow via the heat conductor, the heat-conductor-to-pressure-duct-wall connection and the pressure duct wall.

17 Claims, 6 Drawing Sheets

FIG 9

BRAKING RESISTOR ARRANGEMENT IN A COMPUTED TOMOGRAPHY GANTRY

CROSS-REFERENCE TO RELATED APPLICATION (S)

The present application hereby claims priority under 35 U.S.C. § 119 to German Patent Application No. DE 10 2021 206 842.1, filed on Jun. 30, 2021, the entire contents of which are incorporated herein by reference.

FIELD

Embodiments of the present invention relate to a gantry for a computed tomography device, a method for cooling a first braking resistor of a gantry of a computed tomography device, and a method for disposing a first braking resistor in the gantry of a computed tomography device.

BACKGROUND

In the field of computed tomography, braking resistors are often used within the drive axis of the rotating part (main drive system) for deceleration processes to convert kinetic energy into heat, unless an active regenerative system is installed.

SUMMARY

The inventors have discovered that a central problem here is the heat generated by the braking resistors, which can result in overheating and damage to the braking resistors if the cooling performance is insufficient. It is therefore necessary within the design of the braking resistor assembly, but also in the configuration of the system connectivity, to ensure sufficient heat dissipation.

Heat dissipation from the braking resistors can be accomplished, for example, by transferring heat across the surface of the braking resistors to an airflow. Although this can be implemented for example in the form of passive convection cooling, the cooling performance, i.e. the heat dissipation, is relatively low. However, a higher cooling performance can be realized by active cooling, in particular by virtue of a higher airflow rate and also a defined temperature of the cooling air.

Embodiments of the present invention provide an alternative to conventional cooling concepts for braking resistors in a gantry of a computed tomography device.

Embodiments of the present invention relate to a gantry for a computed tomography device,
  wherein the gantry has a support structure, a rotary or pivot bearing, a rotating frame, a first braking resistor for electromotively braking a rotational movement of the rotating frame, and a heat conductor for dissipating heat from the first braking resistor,
  wherein, via the rotary bearing, the rotating frame is rotatably mounted relative to the support structure about an axis of rotation and has a set of rotating frame components,
  wherein the support structure has a fan for generating an airflow for cooling the set of rotating frame components and a pressure duct for guiding the airflow along at least one flow path,
  wherein the pressure duct has a pressure duct wall disposed between the heat conductor and the airflow
  wherein the heat conductor and the pressure duct wall are interconnected to form a heat-conductor-to-pressure-duct-wall connection that is detachable, form-fitting, planar, and thermally conductive,
  wherein the heat can be transferred from the first braking resistor to the airflow via the heat conductor, the heat-conductor-to-pressure-duct-wall connection and the pressure duct wall.

Thus, the pressure duct wall constitutes a heat sink for transferring heat from the first braking resistor to the airflow.

In particular, it can be provided that the gantry further has a rotary drive, in particular a motor, for electromotively driving the rotational movement of the rotating frame. For example, the gantry can have a motor/bearing unit, wherein the motor/bearing unit has the rotary drive and the rotary bearing.

In addition, it can be provided that the gantry has a converter, in particular a frequency converter, which interacts with the first braking resistor and/or a second braking resistor and/or the rotary drive. For example, the converter can interact with the motor during electromotive driving of the rotational movement of the rotating frame in motor mode. For example, the converter can interact with the motor and the first braking resistor and/or the second braking resistor during electromotive braking of the rotational movement of the rotating frame in regenerative mode.

During electromotive braking, the rotational speed setpoint is reduced by the frequency converter, wherein the motor is operated as a generator. The electrical energy generated by the motor on the basis of the kinetic energy of the rotating frame is transferred to the frequency converter and from there to the first braking resistor and/or the second braking resistor, where it is converted into heat.

For example, the first set of rotating frame components can have at least one X-ray source and/or at least one X-ray detector.

According to an embodiment, the first braking resistor has a housing, wherein the heat conductor has, in particular is, a first wall of the housing of the first braking resistor. The housing of the braking resistor can be an aluminum profile, for example, and form an enclosure for a cassette, wherein the cassette contains a braking resistor wire embedded in sand for example.

An embodiment provides that the first housing wall of the housing of the first braking resistor is attached in a planar manner to the pressure duct wall, in particular is attached in a planar manner to form the heat-conductor-to-pressure-duct-wall connection.

According to an embodiment, the gantry has a second braking resistor for electromotively braking the rotational movement of the rotating frame, wherein the second braking resistor has a housing, wherein the housing of the first braking resistor is disposed between the pressure duct wall and the housing of the second braking resistor,
  wherein the housing of the first braking resistor and the housing of the second braking resistor are interconnected to form a housing-to-housing connection that is detachable, form-fitting, planar, and thermally conductive,
  wherein the heat can be transferred from the second braking resistor to the housing of the first braking resistor via the housing-to-housing connection and can be transferred from there to the airflow via the heat conductor, the heat-conductor-to-pressure-duct-wall connection and the pressure duct wall.

In addition, it can be provided that the heat conductor is also designed to dissipate heat from the second braking resistor and comprises the housing-to-housing connection. The first braking resistor and the second braking resistor can be connected in series or in parallel with one another. In particular, the braking resistors can be designed to be co-extensive and/or stackable.

According to an embodiment, the heat conductor further has a second wall of the housing of the first braking resistor and a first wall of the housing of the second braking resistor,
wherein the second wall of the housing of the first braking resistor is attached in a planar manner to the first wall of the housing of the second braking resistor, in particular attached in a planar manner to form the housing-to-housing connection.

An embodiment provides that the second wall of the housing of the first braking resistor is essentially parallel to the pressure duct wall.

According to an embodiment, the pressure duct wall has a set of holes, wherein the housing of the first braking resistor has a set of holes disposed in a corresponding manner to the set of holes of the pressure duct wall, wherein the heat-conductor-to-pressure-duct-wall connection has a set of screwed connections, wherein each screwed connection of the set of screwed connections is based on a respective screw which is guided through a hole of the set of holes of the first braking resistor and through a hole of the set of holes of the pressure duct wall and engages with a respective internal thread in such a way that said screwed connection causes the housing of the first braking resistor to be pressed against the pressure duct wall.

An embodiment provides that a weld nut containing the internal thread is welded to the pressure duct wall at each hole of the set of holes of the pressure duct wall.

An embodiment provides that the pressure duct wall extends in a planar manner in a plane perpendicular to the axis of rotation.

An embodiment provides that the pressure duct has a set of rotating frame-side openings designed to tap off a rotating frame airflow from the airflow, the rotating frame airflow being provided to cool the set of rotating frame components, wherein the set of rotating frame-side openings has at least one rotating frame-side opening such that the heat-conductor-to-pressure-duct-wall connection is disposed on the at least one flow path downstream of the fan and upstream of the at least one rotating frame-side opening.

Embodiments of the present invention further relate to a computed tomography device having a gantry.

Embodiments of the present invention further relate to a method for cooling a first braking resistor of a gantry of a computed tomography device,
wherein the gantry has a support structure, a rotary bearing, a rotating frame, the first braking resistor, and a heat conductor, wherein, via the rotary bearing, the rotating frame is rotatably mounted relative to the support structure about an axis of rotation and has a set of rotating frame components, wherein the support structure has a fan and a pressure duct, wherein the pressure duct has a pressure duct wall disposed between the heat conductor and the airflow, wherein the heat conductor and the pressure duct wall are interconnected to form a heat-conductor-to-pressure-duct-wall connection that is detachable, form-fitting, planar, and thermally conductive,
the method comprising:
generating an airflow via the fan for cooling the set of rotating frame components,
guiding the airflow via the pressure duct along at least one flow path, and
electromotively braking a rotational movement of the rotating frame via the first braking resistor,
dissipating heat from the first braking resistor via the heat conductor,
transferring the heat from the first braking resistor to the airflow via the heat conductor, the heat-conductor-to-pressure-duct-wall connection and the pressure duct wall.

In an embodiment, after transfer of heat from the first braking resistor to the airflow via the heat conductor, the heat-conductor-to-pressure-duct-wall connection and the pressure duct wall, a rotating frame airflow is tapped off from the airflow, wherein the rotating frame airflow is provided for cooling the set of rotating frame components. In particular, the set of rotating frame components can be cooled via the rotating frame airflow.

Embodiments of the present invention further relate to a method for disposing a first braking resistor in a gantry of a computed tomography device,
wherein the gantry has a support structure, a rotary bearing, a rotating frame, wherein, via the rotary bearing, the rotating frame is rotatably mounted relative to the support structure about an axis of rotation and has a set of rotating frame components, wherein the support structure has a fan for generating an airflow for cooling the set of rotating frame components, and a pressure duct for guiding the airflow along at least one flow path, wherein the pressure duct has a pressure duct wall,
the method comprising:
disposing the first braking resistor for electromotively braking a rotational movement of the rotating frame and a heat conductor for dissipating heat from the first braking resistor in a position relative to the pressure duct wall such that the pressure duct wall is disposed between the heat conductor and the airflow,
interconnecting the heat conductor and the pressure duct wall to form a heat-conductor-to-pressure-duct-wall connection that is detachable, form-fitting, planar and thermally conductive, such that the heat from the first braking resistor can be transferred to the airflow via the heat conductor, the heat-conductor-to-pressure-duct-wall connection and the pressure duct wall.

An embodiment provides that the gantry has a guide element, wherein, when the first braking resistor and the heat conductor are disposed relative to the pressure duct wall, a housing of the first braking resistor is guided via the guide element in a form-fit manner along an attachment direction relative to the pressure duct wall, in particular guided such that the housing of the first braking resistor is secured in a form-fit manner against displacement in a plane perpendicular to the attachment direction relative to the pressure duct wall. The attachment direction can, for example, be perpendicular to the pressure duct wall.

An embodiment provides that a second braking resistor for electromotively braking the rotational movement of the rotating frame is disposed relative to a housing of the first braking resistor such that the housing of the first braking resistor is disposed between the pressure duct wall and a housing of the second braking resistor, wherein the housing of the first braking resistor and the housing of the second braking resistor are interconnected to form a housing-to-housing interconnection which is detachable, form-fitting, planar and heat-conducting, in such a way that the heat can be transferred from the second braking resistor to the housing of the first braking resistor via the housing-to-housing connection and can be transferred from there to the airflow via the heat conductor, the heat-conductor-to-pressure-duct-wall connection and the pressure duct wall.

The pressure duct wall can be made of sheet metal, for example. In particular, the pressure duct wall can be thermally conductive. The pressure duct wall can, for example, be coated with a rustproofing layer, in particular in the form of a paint or a powder coating.

The housing of the first braking resistor and/or the housing of the second braking resistor can be made of sheet metal, for example. The housing of the first braking resistor and/or the housing of the second braking resistor can in particular be thermally conductive. The housing of the first braking resistor and/or the housing of the second braking resistor can, for example, be coated with a rustproofing layer, in particular in the form of a paint or a powder coating.

Optionally, the heat conductor can comprise a heat conduction pad and/or a heat conduction paste, for example in order to provide even better thermal coupling of the first wall of the housing of the first braking resistor to the pressure duct wall and/or in order to provide even better thermal coupling of the housing of the second braking resistor to the housing of the first braking resistor.

One or more embodiments of the described solution enable increased heat dissipation of the braking resistors, which also increases the average power dissipated by the resistor elements. In addition, the higher power dissipation for identical requirements lowers the costs, due to the use of smaller designs. Another advantage of one or more embodiments of the described solution arises from the much lower installation space requirements in the system.

Within the scope of the present invention, features described with respect to different embodiments of the present invention and/or different claim categories (method, use, device, system, arrangement, etc.) may be combined to form further embodiments of the present invention. For example, a claim relating to a device may also be further refined using features described or claimed in connection with a method, and vice versa. Functional features of a method can be implemented by appropriately designed components in question.

BRIEF DESCRIPTION OF THE DRAWINGS

The present invention will now be explained using exemplary embodiments and with reference to the accompanying drawings. The depiction in the figures is schematic, greatly simplified and not necessarily to scale.

DETAILED DESCRIPTION

Figure 1:
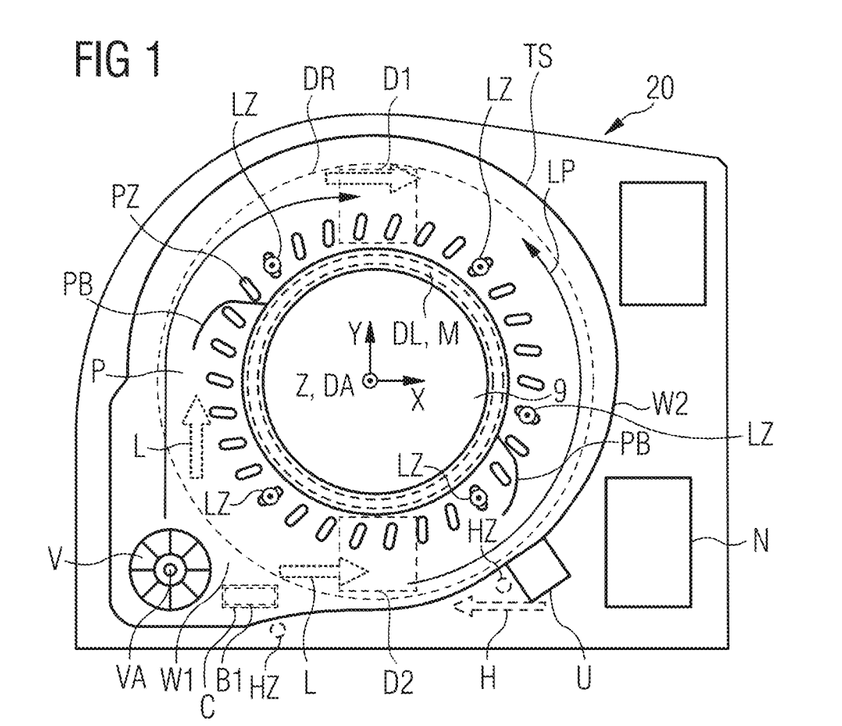
FIG. 1 shows an embodiment of a gantry for a computed tomography device.

FIG. 1 shows a gantry 20 for a computed tomography device,
  wherein the gantry 20 has a support structure TS, a rotary bearing DL, a rotating frame DR, a first braking resistor B1 for electromotively braking a rotational movement of the rotating frame DR, and a heat conductor C for dissipating heat from the first braking resistor B1,
  wherein, via the rotary bearing DL, the rotating frame DR is mounted so as to rotate about an axis of rotation DA relative to the support structure TS and has a set of rotating frame components D1, D2,
  wherein the support structure TS has a fan V for generating an airflow L for cooling the set of rotating frame components D1, D2 and a pressure duct P for guiding the airflow L along at least one flow path LP,
  wherein the pressure duct P has a pressure duct wall W1 disposed between the heat conductor C and the airflow L,
  wherein the heat conductor C and the pressure duct wall W1 are interconnected to form a heat-conductor-to-pressure-duct-wall connection CW which is detachable, form-fitting, planar and thermally conductive,
  wherein the heat can be transferred from the first braking resistor B1 to the airflow L via the heat conductor C, the heat-conductor-to-pressure-duct-wall connection CW and the pressure duct wall W1.

The gantry 20 further has a rotary drive M for electromotively driving the rotational movement of the rotating frame DR, wherein the rotary bearing DL and the rotary drive M together form a motor/bearing unit.

The gantry 20 has a converter U, in particular a frequency converter, which interacts with the first braking resistor B1 and the rotary drive M. The gantry 20 further has a power supply unit N for supplying power in particular to the converter U.

The pressure duct P has a set of rotating frame-side openings PZ designed to tap off a rotating frame airflow LZ from the airflow L, wherein the rotating frame airflow LZ is provided for cooling the set of rotating frame components D1, D2, wherein the set of rotating frame-side openings PZ has at least one rotating frame-side opening such that the heat-conductor-to-pressure-duct-wall connection CW is disposed on the at least one flow path LP downstream of the fan V and upstream of the at least one rotating frame-side opening.

The pressure duct P further has the pressure duct wall W2, which curves around the axis of rotation DA and bounds the pressure duct P in directions extending perpendicularly away from the axis of rotation DA. In principle, it would also be possible for the heat conductor C and the pressure duct wall W2 to be interconnected to form a heat-conductor-to-pressure-duct-wall connection CW which is detachable, form-fitting, planar and thermally conductive, wherein the heat can be transferred from the first braking resistor B1 to the airflow L via the heat conductor C, the heat-conductor-to-pressure-duct-wall connection CW and the pressure duct wall W2.

The pressure duct also has baffles PB for guiding the airflow L. In particular, a baffle PB can be disposed in the region of the heat-conductor-to-pressure-duct-wall connection CW, in particular be disposed perpendicular to the pressure duct wall W1. The baffle PB can thus act as a cooling fin for transferring heat to the airflow L.

Figure 2:
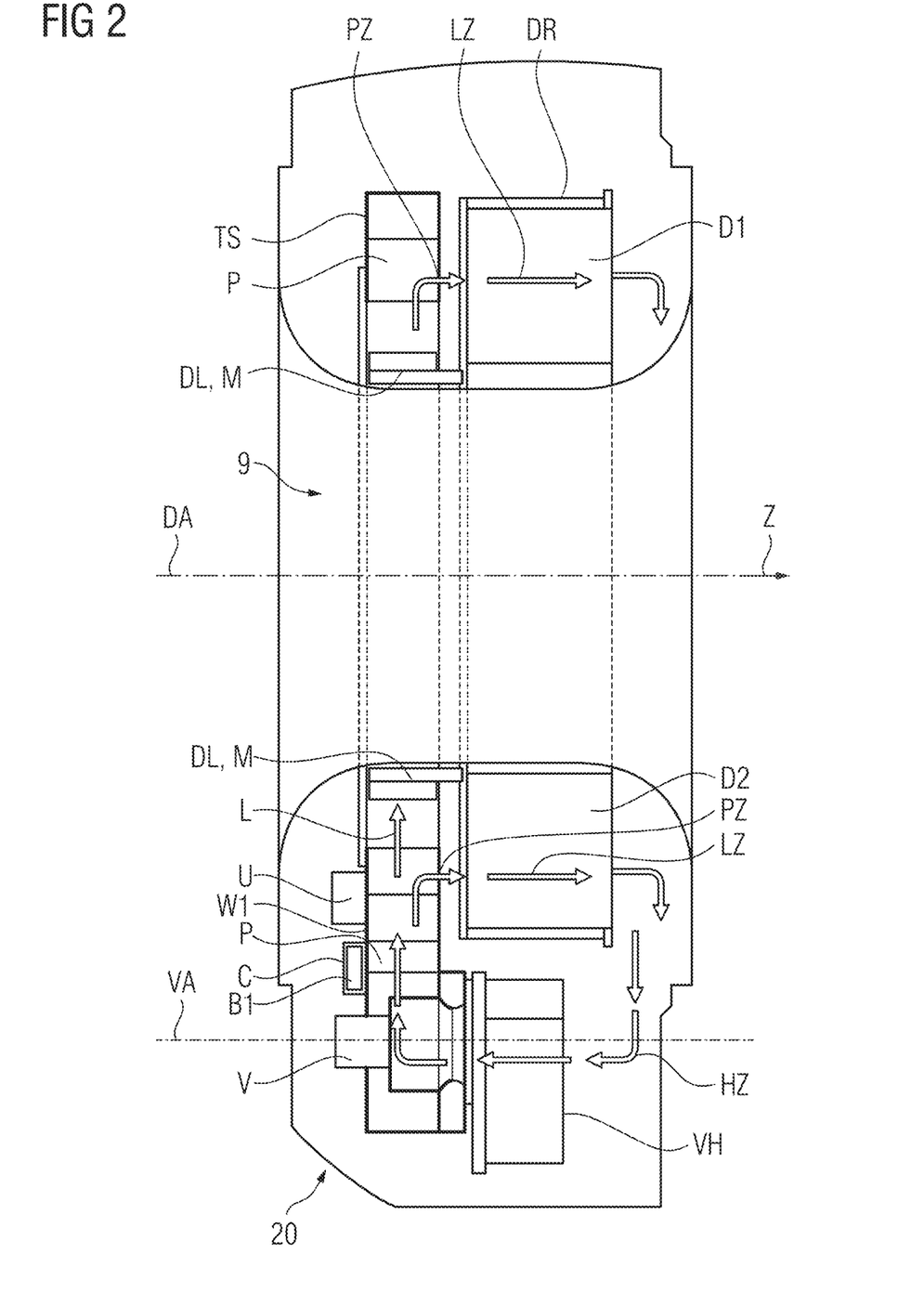
FIG. 2 shows an embodiment of a gantry for a computed tomography device in another view.

FIG. 2 shows a gantry 20 for a computed tomography device in another view. The fan V draws air along the fan axis VA through the heat exchanger VH which cools the incoming air. After transfer of heat from the set of rotating frame components D1, D2, the heated airflow HZ, H flows inside the gantry 20 back to the heat exchanger, forming a closed cooling circuit.

Figure 3:
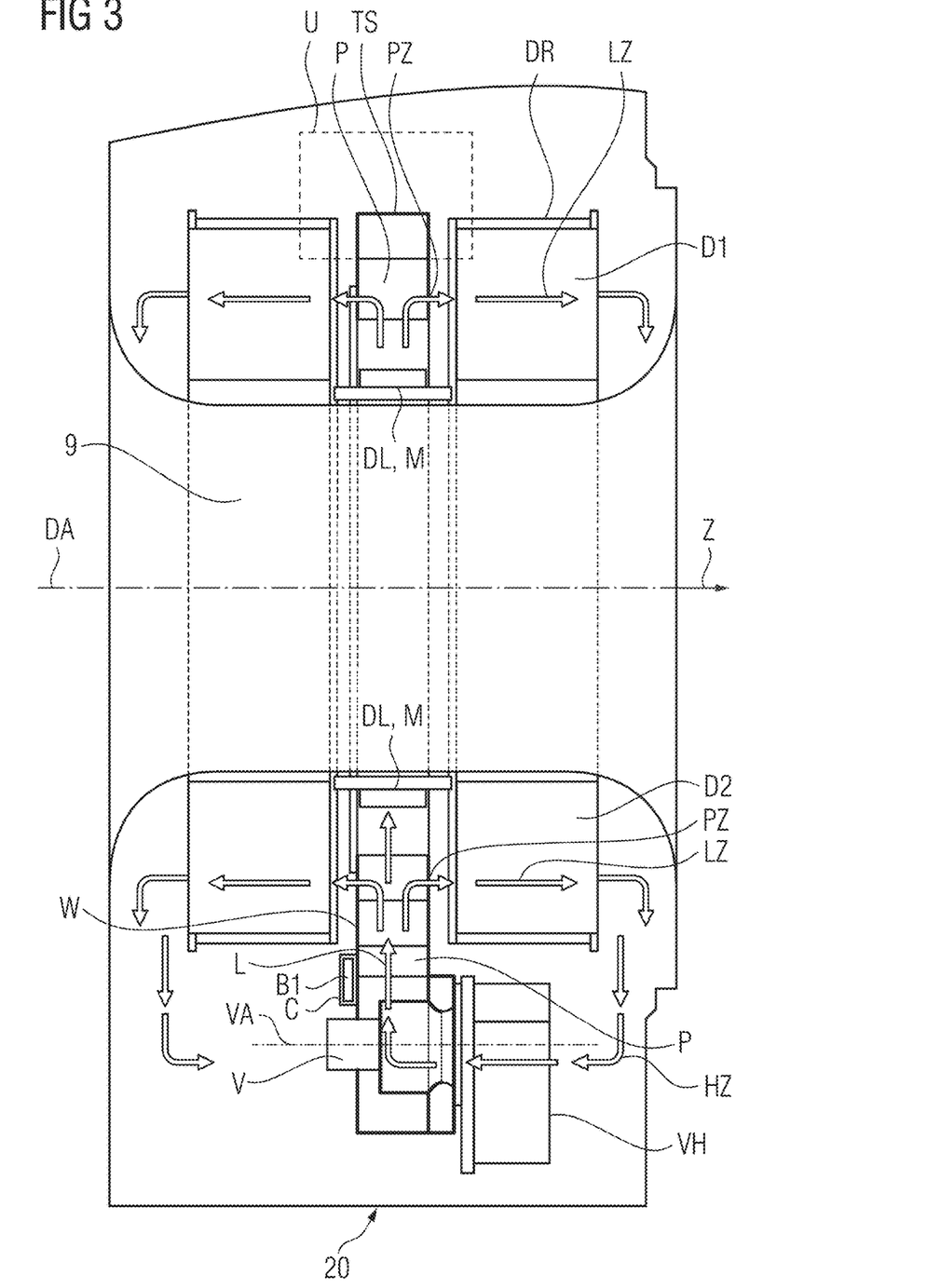
FIG. 3 shows an embodiment of a gantry for a dual-source computed tomography device.

FIG. 3 shows a gantry 20 for a computed tomography device designed as a dual-source computed tomography device. The pressure duct P also has openings in a pressure duct wall parallel to the pressure duct wall W1, so that rotating frame airflows can leave the pressure duct in two opposite directions along the axis of rotation.

Figure 4:
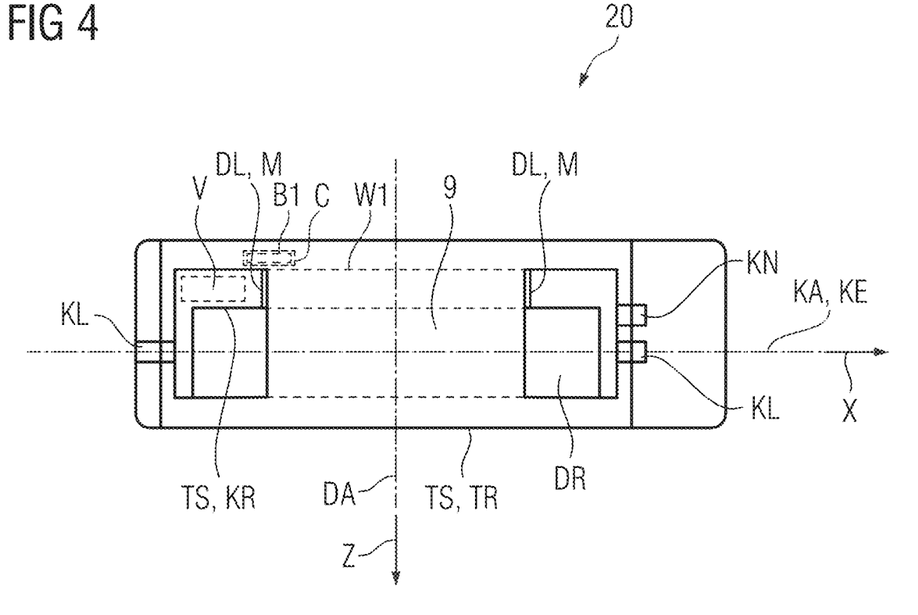
FIG. 4 shows an embodiment of a gantry for a computed tomography device in another view.

FIG. 4 shows a gantry 20 for a computed tomography device in another view. The support structure TS has a tilting frame KR, a tilt bearing KL, a tilt drive KN for driving a tilting motion, and a support frame TR, wherein, via the tilt bearing KL, the tilting frame KR is mounted so as to tilt about a tilt axis KA relative to the support frame TR, wherein the tilting frame KR contains the fan V and the pressure duct P, wherein, via the rotary bearing DL, the rotating frame DR is mounted so as to rotate about a rotational axis DA relative to the tilting frame KR.

The pressure duct wall W1 extends in a planar manner in a plane perpendicular to the axis of rotation DA and parallel to the tilting plane KE in which the tilting axis KA lies. The axis of rotation DA is parallel to the direction Z. The tilt axis KA is parallel to the direction X.

Figure 5:
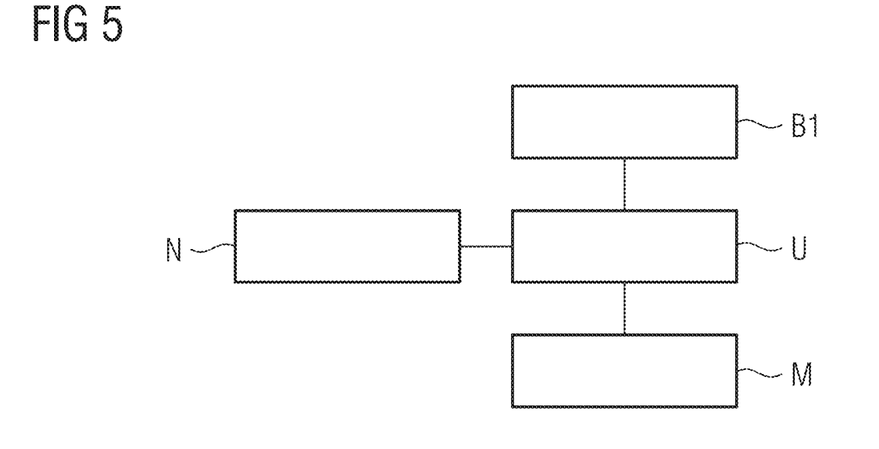
FIG. 5 shows a schematic circuit with a first braking resistor, according to an embodiment.

FIG. 5 shows a schematic circuit with a first braking resistor B1, a converter U, a rotary drive M and a power supply unit N.

Figure 6:
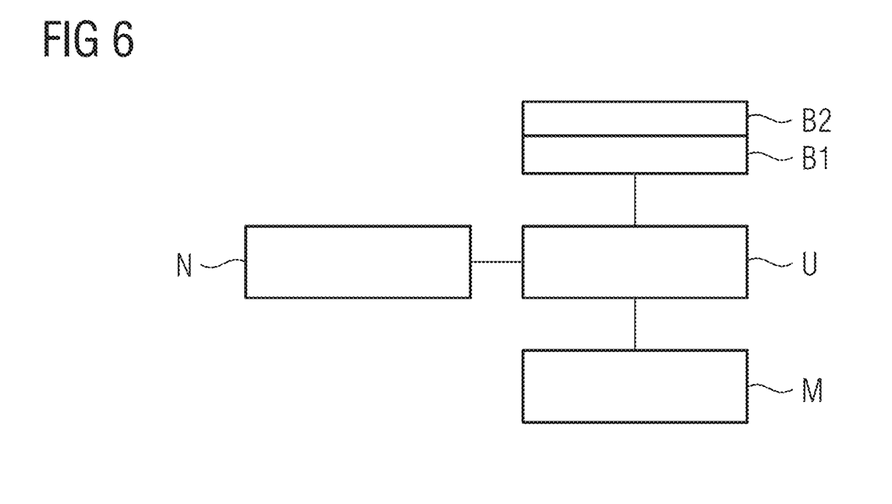
FIG. 6 shows a schematic circuit with a first braking resistor and a second braking resistor, according to an embodiment.

FIG. 6 shows a schematic circuit with a first braking resistor B1, a second braking resistor B2, a converter U, a rotary drive M and a power supply unit N.

Figure 7:
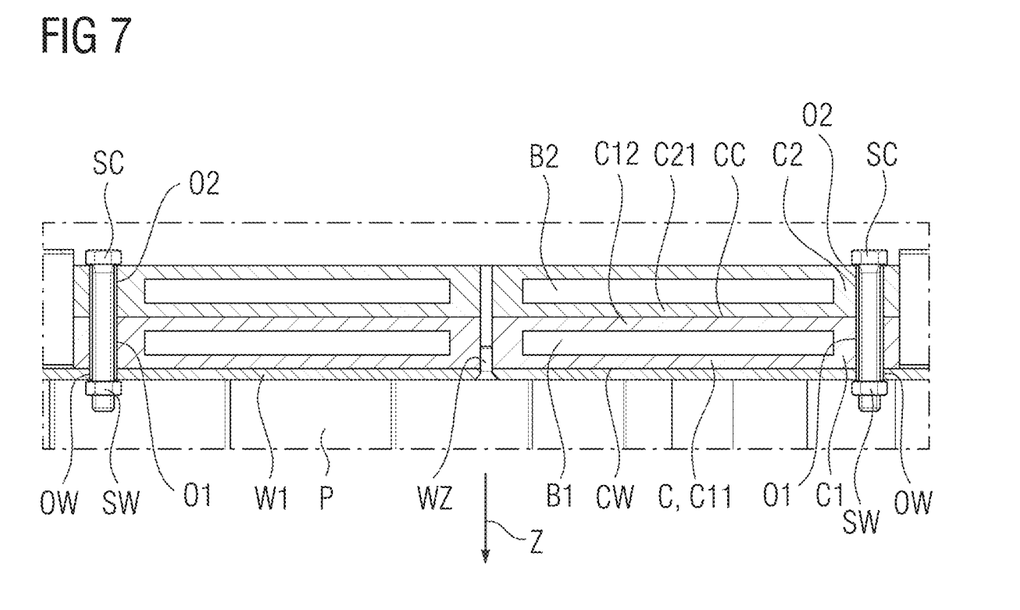
FIG. 7 shows an embodiment of a braking resistor arrangement on a pressure duct wall.

FIG. 7 shows a braking resistor arrangement on a pressure duct wall. The first braking resistor B1 has a housing C1, wherein the heat conductor C has a first housing wall C11 of the housing C1 of the first braking resistor B1. The first housing wall C11 of the housing C1 of the first braking resistor B1 is attached in a planar manner to the pressure duct wall W1, in particular attached in a planar manner to form the heat-conductor-to-pressure-duct-wall connection CW.

The gantry 20 has a second braking resistor B2 for braking the rotational movement of the rotating frame DR via an electric motor, wherein the second braking resistor B2 has a housing C2, wherein the housing C1 of the first braking resistor B1 is disposed between the pressure duct wall W1 and the housing C2 of the second braking resistor B2, wherein the housing C1 of the first braking resistor B1 and the housing C2 of the second braking resistor B2 are interconnected to form a housing-to-housing connection CC which is detachable, form-fitting, planar and thermally conductive, wherein the heat can be transferred from the second braking resistor B2 to the housing C1 of the first braking resistor B1 via the housing-to-housing connection CC and can be transferred from there to the airflow L via the heat conductor C, the heat-conductor-to-pressure-duct-wall connection CW and the pressure duct wall W1. The heat conductor C is additionally designed to dissipate heat from the second braking resistor B2 and has the housing-to-housing connection CC.

The heat conductor C additionally has a second housing wall C12 of the housing C1 of the first braking resistor B1 and a first housing wall C21 of the housing C2 of the second braking resistor B2, wherein the second housing wall C12 of the housing C1 of the first braking resistor B1 is attached in a planar manner to the first housing wall C21 of the housing C2 of the second braking resistor B2, in particular forming the housing-to-housing connection CC in a planar manner. The second housing wall C12 of the housing C1 of the first braking resistor B1 is parallel to the pressure duct wall W1. The first housing wall C21 of the housing C2 of the second braking resistor B2 is parallel to the first housing wall C11 of the housing C1 of the first braking resistor B1. As a result, the braking resistors can be stacked one on top of the other.

The pressure duct wall W1 has a set of holes OW, wherein the housing C1 of the first braking resistor B1 has a set of holes O1 disposed correspondingly to the set of holes OW of the pressure duct wall W1, wherein the heat-conductor-to-pressure-duct-wall connection CW has a set of screwed connections, wherein each screwed connection of the set of screwed connections is based on a respective screw SC which is guided through a hole of the set of holes O1 of the first braking resistor B1 and through a hole of the set of holes OW of the pressure duct wall W1 and engages with an internal thread in each case in such a way that said screwed connection causes the housing C1, in particular the first housing wall C11 of the housing C1, of the first braking resistor B1 to be pressed against the pressure duct wall W1.

The housing C2 of the second braking resistor B2 has a set of holes O2 disposed correspondingly to the set of holes OW of the pressure duct wall W1. The holes are through-holes in each case.

At each hole of the set of holes OW of the pressure duct wall W1, a weld nut SW, which has the internal thread, is welded to the pressure duct wall W1. The weld nut SW is disposed between the pressure duct wall W1 and the airflow L. The pressure duct wall W1 and the braking resistors are disposed between the weld nut SW and the head of the screw SC.

Figure 8:
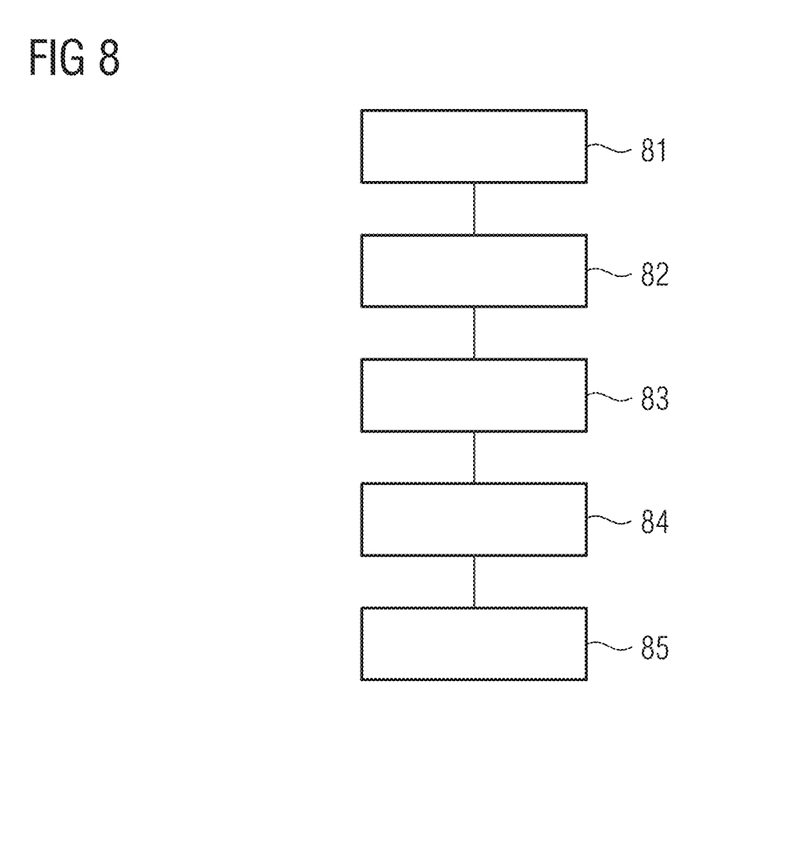
FIG. 8 shows a flowchart of a method for cooling a first braking resistor of a gantry of a computed tomography device, according to an embodiment.

FIG. 8 shows a flow diagram of a method for cooling a first braking resistor B1 of a gantry 20 of a computed tomography device,
   wherein the gantry 20 has a support structure TS, a rotary bearing DL, a rotating frame DR, the first braking resistor B1, and a heat conductor C, wherein, via the rotary bearing DL, the rotating frame DR is rotatably mounted about an axis of rotation DA relative to the support structure TS and has a set of rotating frame components D1, D2, wherein the support structure TS has a fan V and a pressure duct P, wherein the pressure duct P has a pressure duct wall W1 disposed between the heat conductor C and the airflow L, wherein the heat conductor C and the pressure duct wall W1 are interconnected to form a heat-conductor-to-pressure-duct-wall connection CW which is detachable, form-fitting, planar and thermally conductive,
   the method comprising:
   generating 81 an airflow L via the fan V for cooling the set of rotating frame components D1, D2,
   guiding 82 of the airflow L via the pressure duct P along at least one flow path LP,
   electromotive braking 83 of a rotational movement of the rotating frame DR via the first braking resistor B1,
   dissipation 84 of heat from the first braking resistor B1 via the heat conductor C,
   transfer 85 of the heat from the first braking resistor B1 to the airflow L via the heat conductor C, the heat-conductor-to-pressure-duct-wall connection CW and the pressure duct wall W1.

After transfer 85 of the heat from the first braking resistor B1 to the airflow L via the heat conductor C, the heat-conductor-to-pressure-duct-wall connection CW and the pressure duct wall W1, a rotating frame airflow LZ is tapped off from the airflow L, wherein the rotating frame airflow LZ is provided for cooling the set of rotating frame components D1, D2. The rotating frame airflow LZ is used to cool the rotating frame components D1, D2.

Figure 9:
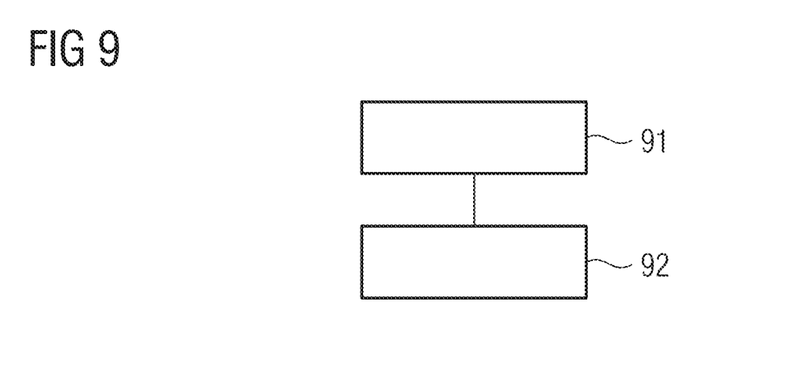
FIG. 9 shows a flowchart of a method for disposing a first braking resistor in a gantry of a computed tomography device, according to an embodiment.

FIG. 9 shows a flowchart of a method for disposing a first braking resistor B1 in a gantry 20 of a computed tomography device, wherein the gantry 20 has a support structure TS, a rotary bearing DL and a rotating frame DR, wherein the rotating frame DR is rotatably mounted about an axis of rotation DA relative to the support structure TS via the rotary bearing DL and has a set of rotating frame components D1, D2, wherein the support structure TS has a fan V for generating an airflow L for cooling the set of rotating frame components D1, D2, and a pressure duct P for guiding the airflow L along at least one flow path LP, wherein the pressure duct P has a pressure duct wall W1, the method comprising:

positioning 91 of the first braking resistor B1 for electromotively braking a rotational movement of the rotating frame DR, and of a heat conductor C for dissipating heat from the first braking resistor B1, relative to the pressure duct wall W1, such that the pressure duct wall W1 is disposed between the heat conductor C and the airflow L, interconnecting 92 the heat conductor C and the pressure duct wall W1 to form a heat-conductor-to-pressure-duct-wall connection CW that is detachable, form-fitting, planar and thermally conductive, such that the heat can be transferred from the first braking resistor B1 to the airflow L via the heat conductor C, the heat-conductor-to-pressure-duct-wall connection CW and the pressure duct wall W1.

The gantry 20 has a guide element WZ in the form of a bolt, wherein on positioning 91 of the first braking resistor B1 and the heat conductor C relative to the pressure duct wall W1, a housing C1 of the first braking resistor B1 is guided in a form-fit manner via the guide element WZ along an attachment direction relative to the pressure duct wall W1, in particular guided in such a way that the housing C1 of the first braking resistor B1 is secured in a form-fit manner against displacement in a plane perpendicular to the attachment direction relative to the pressure duct wall W1, wherein the attachment direction is perpendicular to the pressure duct wall W1.

A second braking resistor B2 for electromotively braking the rotational movement of the rotating frame DR is positioned relative to a housing C1 of the first braking resistor B1 such that the housing C1 of the first braking resistor B1 is disposed between the pressure duct wall W1 and a housing C2 of the second braking resistor B2, wherein the housing C1 of the first braking resistor B1 and the housing C2 of the second braking resistor B2 are interconnected to form a housing-to-housing connection CC which is detachable, form-fitting, planar and heat-conducting, in such a way that the heat can be transferred from the second braking resistor B2 to the housing C1 of the first braking resistor B1 via the housing-to-housing connection CC and can be transferred from there to the airflow L via the heat conductor C, the heat-conductor-to-pressure-duct-wall connection CW and the pressure duct wall W1.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element (s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A gantry for a computed tomography device, the gantry comprising:
   a support structure;
   a rotary bearing;
   a rotating frame;
   a first braking resistor configured to electromotively brake a rotational movement of the rotating frame;
   a second braking resistor configured to electromotively brake the rotational movement of the rotating frame; and
   a heat conductor configured to dissipate heat from the first braking resistor;
   wherein the rotating frame is rotatably mounted about an axis of rotation relative to the support structure via the rotary bearing, and the rotating frame has a set of rotating frame components;
   wherein the support structure has a fan configured to generate an airflow to cool the set of rotating frame components, and a pressure duct to guide the airflow along at least one flow path;
   wherein the pressure duct has a pressure duct wall between the heat conductor and the airflow;
   wherein the heat conductor and the pressure duct wall are interconnected to form a heat-conductor-to-pressure-duct-wall connection that is detachable, form-fitting, planar and thermally conductive;
   wherein the heat is transferrable from the first braking resistor to the airflow via the heat conductor, the heat-conductor-to-pressure-duct-wall connection and the pressure duct wall;
   wherein the first braking resistor has a housing;
   wherein the heat conductor includes a first housing wall of the housing of the first braking resistor;
   wherein the second braking resistor has a housing;
   wherein the housing of the first braking resistor is between the pressure duct wall and the housing of the second braking resistor;
   wherein the heat conductor includes a second housing wall of the housing of the first braking resistor and a first housing wall of the housing of the second braking resistor; and
   wherein the second housing wall of the housing of the first braking resistor is attached to the first housing wall of the housing of the second braking resistor in a planar manner.

2. The gantry as claimed in claim 1,
   wherein the first housing wall of the housing of the first braking resistor is attached to the pressure duct wall in a planar manner.

3. The gantry as claimed in claim 2, further comprising:
   wherein the housing of the first braking resistor and the housing of the second braking resistor are interconnected to form a housing-to-housing connection which is detachable, form-fitting, planar and thermally conductive, and
   wherein the heat is transferrable from the second braking resistor to the housing of the first braking resistor via the housing-to-housing connection, and then from the housing of the first braking resistor to the airflow via the heat conductor, the heat-conductor-to-pressure-duct-wall connection and the pressure duct wall.

4. The gantry as claimed in claim 3,
   wherein the second housing wall of the housing of the first braking resistor is substantially parallel to the pressure duct wall.

5. The gantry as claimed in claim 1, further
   wherein the housing of the first braking resistor and the housing of the second braking resistor are interconnected to form a housing-to-housing connection which is detachable, form-fitting, planar and thermally conductive, and
   wherein the heat is transferrable from the second braking resistor to the housing of the first braking resistor via the housing-to-housing connection, and then from the housing of the first braking resistor to the airflow via the heat conductor, the heat-conductor-to-pressure-duct-wall connection and the pressure duct wall.

6. The gantry as claimed in claim 1,
   wherein the second housing wall of the housing of the first braking resistor is substantially parallel to the pressure duct wall.

7. The gantry as claimed in claim 1,
   wherein the pressure duct wall extends in a planar manner in a pressure duct wall plane perpendicular to the axis of rotation.

8. The gantry as claimed in claim 1,
wherein the pressure duct has a set of rotating frame-side openings configured to tap off a rotating frame airflow from the airflow,
wherein the rotating frame airflow is provided to cool the set of rotating frame components, and
wherein the set of rotating frame-side openings has at least one rotating frame-side opening such that the heat-conductor-to-pressure-duct-wall connection is on the at least one flow path downstream of the fan and upstream of the at least one rotating frame-side opening.

9. A computed tomography device having the gantry as claimed in claim 1.

10. The gantry as claimed in claim 1
wherein the pressure duct wall has a set of holes,
wherein the housing of the first braking resistor has a set of holes disposed correspondingly to the set of holes of the pressure duct wall, and
wherein the heat-conductor-to-pressure-duct-wall connection has a set of screwed connections, each screwed connection of the set of screwed connections being based on a respective screw, which is guided through a hole of the set of holes of the first braking resistor and through a hole of the set of holes of the pressure duct wall, and engages with a respective internal thread such that the screwed connection causes the housing of the first braking resistor to be pressed against the pressure duct wall.

11. A gantry for a computed tomography device, the gantry comprising:
a support structure;
a rotary bearing;
a rotary frame;
a first braking resistor configured to electromotively brake a rotational movement of the rotating frame;
a heat conductor configured to dissipate heat from the first braking resistor;
wherein the rotating frame is rotatably mounted about an axis of rotation relative to the support structure via the rotary bearing, and the rotating frame has a set of rotating frame components;
wherein the support structure has a fan configured to generate an airflow to cool the set of rotating frame components, and a pressure duct to guide the airflow along at least one flow path;
wherein the pressure duct has a pressure duct wall between the heat conductor and the airflow;
wherein the heat conductor and the pressure duct wall are interconnected to form a heat-conductor-to-pressure-duct-wall connection that is detachable, form fitting, planar and thermally conductive;
wherein the heat is transferrable from the fist braking resistor to the airflow via the heat conductor, the heat-conductor-to-pressure-duct-wall connection and the pressure duct wall;
wherein the first braking resistor has a housing;
wherein the heat conductor includes a first housing wall of the housing of the first braking resistor;
wherein the pressure duct wall has a set of holes,
wherein the housing of the first braking resistor has a set of holes disposed correspondingly to the set of holes of the pressure duct wall,
wherein the heat-conductor-to-pressure-duct-wall connection has a set of screwed connections, each screwed connection of the set of screwed connections being based on a respective screw, which is guided through a hole of the set of holes of the first braking resistor and through a hole of the set of holes of the pressure duct wall and engages with a respective internal thread such that the screwed connection causes the housing of the first braking resistor to be pressed against the pressure duct wall.

12. The gantry as claimed in claim 11,
wherein a weld nut having the respective internal thread is welded to the pressure duct wall at each hole of the set of holes of the pressure duct wall.

13. A method for cooling a first braking resistor of a gantry of a computed tomography device, the gantry including a support structure, a rotary bearing, a rotating frame, the first braking resistor, a second braking resistor and a heat conductor, wherein the rotating frame is rotatably mounted via the rotary bearing about an axis of rotation relative to the support structure, and the rotating frame has a set of rotating frame components, wherein the support structure has a fan and a pressure duct, wherein the pressure duct has a pressure duct wall between the heat conductor and an airflow, wherein the heat conductor and the pressure duct wall are interconnected to form a heat-conductor-to-pressure-duct-wall connection which is detachable, form-fitting, planar and thermally conductive, and wherein the method comprises:
generating an airflow via the fan for cooling the set of rotating frame components;
guiding the airflow via the pressure duct along at least one flow path;
electromotive braking of a rotational movement of the rotating frame via the first braking resistor and the second resistor;
dissipating heat from the first braking resistor via the heat conductor; and
transferring the heat from the first braking resistor to the airflow via the heat conductor, the heat-conductor-to-pressure-duct-wall connection and the pressure duct wall; wherein
the first braking resistor has a housing,
the heat conductor includes a first housing wall of the housing of the first braking resistor,
the second braking resistor has a housing
the housing of the first braking resistor is between the pressure duct wall and the housing of the second braking resistor,
the heat conductor includes a second housing wall of the housing of the first braking resistor and a first housing wall of the housing of the second braking resistor, and
the second housing wall of the housing of the first braking resistor is attached to the first housing wall of the housing of the second braking resistor in a planar manner.

14. The method as claimed in claim 13, wherein after transferring of the heat from the first braking resistor to the airflow via the heat conductor, the heat-conductor-to-pressure-duct-wall connection and the pressure duct wall, the method comprises:
tapping off a rotating frame airflow from the airflow, wherein the rotating frame airflow is provided for cooling the set of rotating frame components.

15. A method for arranging a first braking resistor in a gantry of a computed tomography device, the gantry including a support structure, a rotary bearing and a rotating frame, wherein the rotating frame is rotatably mounted via the rotary bearing about an axis of rotation relative to the support structure, and the rotating frame has a set of rotating frame components, wherein the support structure has a fan for generating an airflow for cooling the set of rotating frame components and a pressure duct for guiding the airflow along at least one flow path, wherein the pressure duct has a pressure duct wall, and wherein the method comprises:

positioning the first braking resistor for electromotively braking a rotational movement of the rotating frame, and positioning a heat conductor for dissipating heat from the first braking resistor relative to the pressure duct wall such that the pressure duct wall is between the heat conductor and the airflow; and     interconnecting the heat conductor and the pressure duct wall to form a heat-conductor-to-pressure-duct-wall connection which is detachable, form-fitting, planar and thermally conductive, such that the heat is transferrable from the first braking resistor to the airflow via the heat conductor, the heat-conductor-to-pressure-duct-wall connection and the pressure duct wall.

16. The method as claimed in claim 15,
wherein the gantry includes a guide element, and
wherein on positioning the first braking resistor and the heat conductor relative to the pressure duct wall, a housing of the first braking resistor is guided in a form-fit manner via the guide element along an attachment direction relative to the pressure duct wall.

17. The method as claimed in claim 15, further comprising:

positioning a second braking resistor relative to a housing of the first braking resistor such that the housing of the first braking resistor is between the pressure duct wall and a housing of the second braking resistor, the second braking resistor being for electromotively braking the rotational movement of the rotating frame; and     wherein the housing of the first braking resistor and the housing of the second braking resistor are interconnected to form a housing-to-housing connection that is detachable, form-fitting, planar and heat-conducting, such that the heat is transferrable from the second braking resistor to the housing of the first braking resistor via the housing-to-housing connection and from the housing of the first braking resistor to the airflow via the heat conductor, the heat-conductor-to-pressure-duct-wall connection and the pressure duct wall.

\* \* \* \* \*